(12) United States Patent
Thomas

(10) Patent No.: US 7,377,493 B2
(45) Date of Patent: May 27, 2008

(54) FRAGRANCING SYSTEM AND METHOD

(75) Inventor: Cheriyan B. Thomas, New Albany, OH (US)

(73) Assignee: Innovative Product Management, LLC, Columbus, OH (US)

(*) Notice: Subject to any disclaimer, the term of this patent is extended or adjusted under 35 U.S.C. 154(b) by 442 days.

(21) Appl. No.: 11/029,955

(22) Filed: Jan. 5, 2005

(65) Prior Publication Data

US 2006/0145368 A1    Jul. 6, 2006

(51) Int. Cl.
*B01F 3/04* (2006.01)

(52) U.S. Cl. .............. 261/30; 261/121.1; 261/DIG. 88; 261/DIG. 89; 422/124

(58) Field of Classification Search ............ 261/30, 261/115, 116, 118, 121.1, 142, DIG. 88, 261/DIG. 89; 422/124, 125; 392/394, 403
See application file for complete search history.

(56) References Cited

U.S. PATENT DOCUMENTS

| | | | |
|---|---|---|---|
| 1,210,772 A | 1/1917 | Duetsch | |
| 2,858,429 A | 2/1952 | Boe | |
| 3,860,401 A * | 1/1975 | Clark et al. | 95/198 |
| 4,399,942 A | 8/1983 | Chand | |
| 4,407,585 A | 10/1983 | Hartford et al. | |
| 4,953,763 A | 9/1990 | Kierum et al. | |
| 4,989,547 A | 2/1991 | Eaton | |
| 5,156,334 A | 10/1992 | Kimbell et al. | |
| 5,437,410 A | 8/1995 | Babasade | |
| 5,858,313 A | 1/1999 | Park et al. | |
| 6,413,302 B1 | 7/2002 | Harrison et al. | |
| 6,443,434 B1 * | 9/2002 | Prather | 261/26 |
| 6,592,104 B2 | 7/2003 | Cox | |

* cited by examiner

*Primary Examiner*—Robert A Hopkins
(74) *Attorney, Agent, or Firm*—Mueller Smith

(57) ABSTRACT

System and method for emanating fragrance vapor into a region. Fragrance liquid within a receptacle exhibits a liquid phase-vapor phase interface surface when in a quiescent state. Utilizing sub-pressure generators such as fan driven systems, the pressure above the interface is lowered to promote the escape of vapor molecules for dissemination into the atmosphere. The surface area of the fragrance fluid may be increased through the use of a bubbling technique to derive an effective area permitting a larger vapor molecule escape.

26 Claims, 4 Drawing Sheets

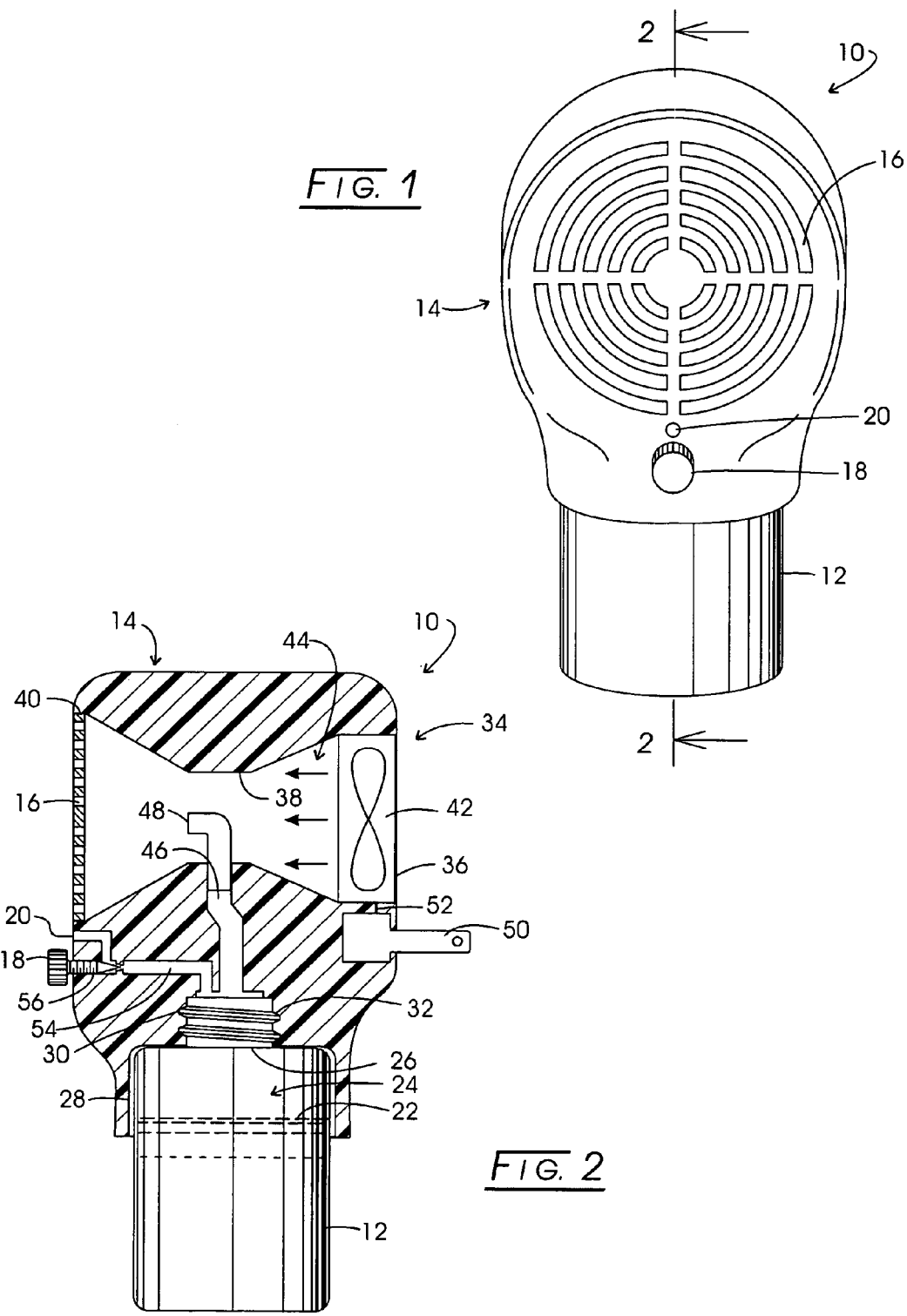

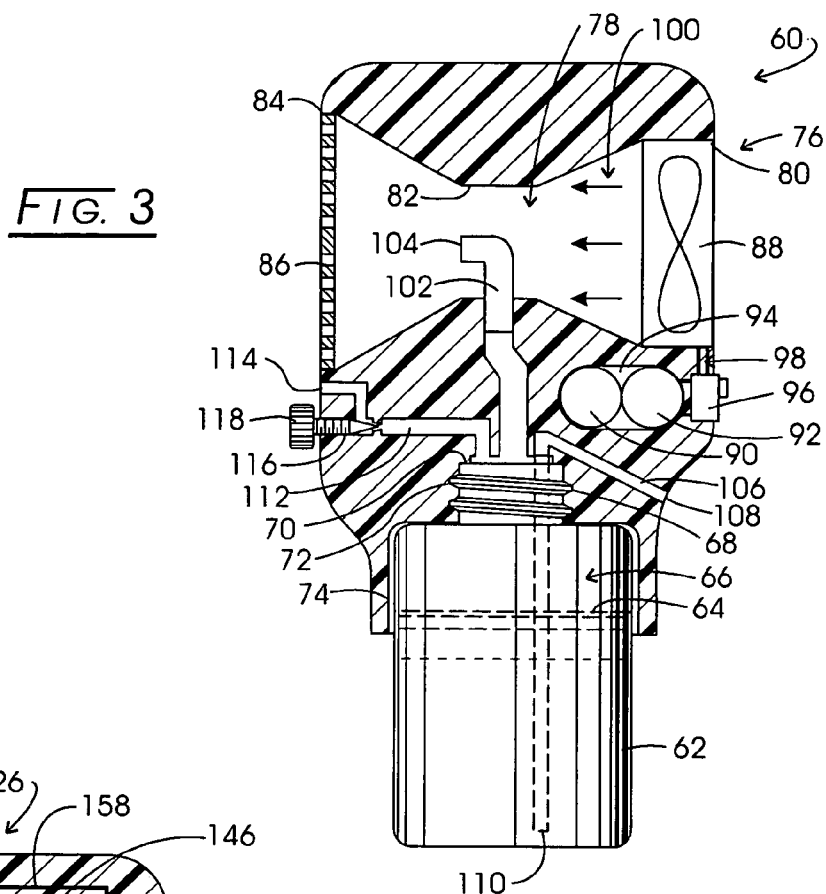
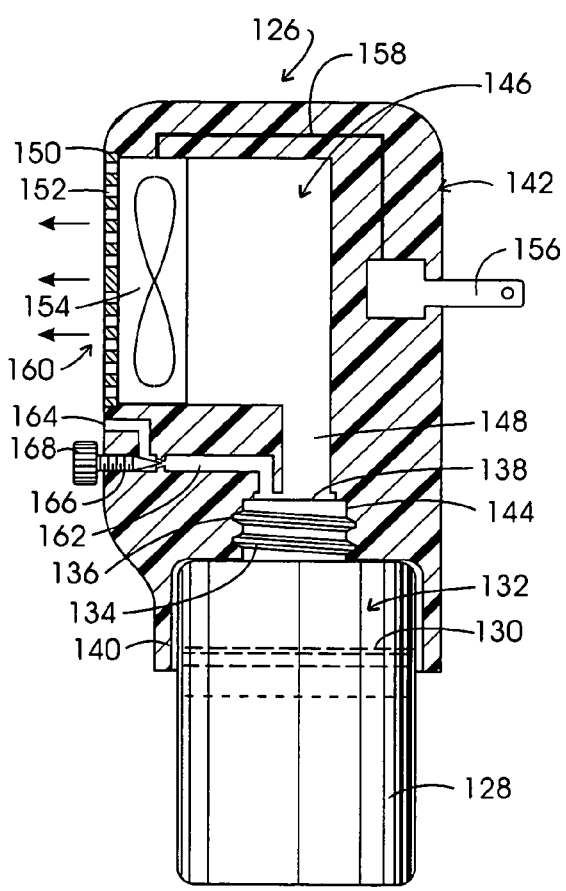

FRAGRANCING SYSTEM AND METHOD

CROSS-REFERENCE TO RELATED APPLICATIONS

STATEMENT REGARDING FEDERALLY SPONSORED RESEARCH

Not applicable.

BACKGROUND OF THE INVENTION

Humankind has used, studied and developed fragrances from ancient times. As early as 4,00 B.C., fragrant substances were burned in China, Arabia and Egypt. Thus, the term "perfume" derives from the Latin phrase "per fumum" meaning "through smoke". Although perfume in the modern cosmetic sense of an alcohol-based solution did not exist in ancient times, evidence of the practice of fumigation with incense combining wood, spice, fruit or resin with a heat source has been found in the hieroglyphics discovered at Edfou and Philae. In his works "Canon Medicinae" and "Treatise About the South" Avicenna (880-1037 A.D.), the physician and mystic mentioned many aromatic resins, such as frankincense, storax, galbanum, ambergris, asant and myrrh, all noted for their healing properties.

While the first alcohol-based perfume was developed for Queen Elizabeth of Hungary in 1370, modern perfumery is considered to have begun in 1806 with the marketing of Eau de Cologne by Jean Maria Farina. His formula consisted of an alcohol-water base scented with an oil composed of neroli, bergamot, rosemary and lemon. The building blocks of all fragrances are the essential oils extracted from flowers, grasses, seeds, leaves, roots, barks, fruits, mosses and resins. Important advancement in fragrances commenced in the nineteenth century with the emergence of organic chemistry, allowing investigators to isolate fragrant molecules and reproduce them synthetically. Synthetics (aroma chemicals) have enabled the replication of scents from flowers, like lilac and lily of the valley that cannot be captured any other way. Fragrance in its most basic form is a molecular composition of carbon, oxygen, hydrogen, nitrogen, and sulphur. When exposed to light or heat that chemical structure can deteriorate.

In the nineteenth century perfumer or "nose" Septimus Piésse implemented a classification system for perfume which remains today. That system corresponds to the musical scale wherein a fragrance composition contains individual notes or essences. The term "notes" can refer to a single ingredient such as jasmine, frankincense or lemon, but may also refer to a perfume's phase or a fragrant blend of ingredients that combine to give a fragrance its top, middle, or base notes. The term "common thread" describes a perfume's ability to flow from one phase to another in a cohesive rather than a discordant fashion. A perfumes "octave" refers to the height of a particular odor or ingredient as it makes it presence known during the drydown process. In 1923, Poucher added to the work of Piésse in publishing a classification method looking to a fragrant ingredient's evaporation rate based upon an overall scale of 1 to 100. In the modern day a perfumer may compose from a repertoire of over 2000 notes. The Société francaise des Parfumeurs has published a perfume classification listing: the citrus family; the floral family; the fern family; the chypre family; the woody family; the oriental family; and the leather family.

The olfactory reaction to a perfume is to its vapor. When encountering the nose, the vapor is warmed, humidified and channeled to the olfactory epithelium. The olfactory sensory cells have cilia with receptor sites that capture and bind the vapor molecules. How those vapor molecules are translated by the receptors into a smell remains a matter of conjecture. Recently, a vibrational theory has arisen wherein the molecules comprising the scent vapors vibrate and switch on the receptors which, in turn, communicate with the limbic system, the seat of emotion and memory in the brain.

See generally:

Newman, "Perfume, The Art and Science of Scent", National Geographic Society, Washington, D.C., 1998.

Booth, "Perfumes, Splashes & Colognes", Storey Publishing, Pownal, Vt., 1997.

Fischer-Rizzi, "The Complete Incense Book", Sterling Publishing Company, New York, N.Y. 1996.

Pavia, "The World of Perfume", Knickerbocker Press, New York, N.Y., 1995.

The present day fragrancing industry maintains two general endeavors, one being personal or cosmetic perfumes typically marketed in artistic containers, and fragrances combined with living space emission devices. The latter devices include incense burners, candles, oil warmers and generally three categories of continuous action fluid dispensers. One of those three categories involves the utilization of a wick which protrudes from a bottle. The wick can be of various diameters or heights. This wick can also be heated using, generally, a resistor in a ceramic housing, the heating of the wick tending to enhance the drawing of fragrance liquid from some reservoir. The second device is one employing a nebulizer with an atomized particle size discriminator function. A third uses a spray nozzle similar to ones employed by an aerosol or a cologne spray with an automated/timed plunger that depresses the spray nozzle periodically, thereby atomizing the liquid. The atomized particles of the fragrance fluid can be observed emanating from a nozzle and thus vaporize into the atmosphere from that condition. With any of the emanating device approaches the liquid fragrance involved may be combined with a solvent to weigh down or dilute the fragrance in order to decrease the evaporation characteristics. In general that solvent is a glycol with an emulsifier, for example, a glycol ether marketed under the trade designation "DOWANOL". Typically, the fragrance is combined in a 1:1 ratio with a solvent, an arrangement adding to the cost of the fragrance formulation. While the heated wick based devices are inexpensive, as noted above, the heating of fragrances may be deleterious. On the other hand, the nebulizing devices can be comparatively expensive. For either approach, typically a duty cycle is involved in device operation to avoid overwhelming the living space with fragrance vapor.

BRIEF SUMMARY OF THE INVENTION

The present invention is addressed to a fragrancing system and method wherein the evaporation of vapor molecules from the surface of a fragrance liquid reservoir is enhanced without resort to mechanical atomization or nebulization techniques and without resort to wicking procedures. This fragrance emanating approach reduces pressure at the fragrance fluid surface while removing vapor molecules thereabove to enhance evaporation into a vapor phase. Vapor evaporation additionally may be enhanced by increasing the area of the liquid-vapor surface. While such a surface area increase does not effect vapor pressure, it affords more opportunity for the vapor molecule to escape. Such a surface area increase is produced by developing bubbles within an otherwise quiescent fragrance liquid volume to evolve a liquid-vapor interface of an expanded surface within the body of the liquid referred to as a surface effect or surface effective area.

An advantage in terms of cost of this evaporation-based system resides in the elimination of otherwise necessary evaporation-limiting agents such as glycol ether solvents which would otherwise work against the precepts of the invention.

As another feature, the invention presents a system for emanating fragrance vapor into a region exhibiting a given atmospheric pressure. A receptacle is provided having an internal cross-section defining liquid-vapor interface area. A fragrance liquid phase is carried by the receptacle which has a liquid surface corresponding, in a quiescent state with the interface area and defining a vapor volume above it. A sub-pressure generator is connected in gas flow communication with the vapor volume and is energizable to derive a lowered pressure below the given atmospheric pressure at the liquid surface effective to enhance the evaporative generation of a vapor phase above the liquid surface while extracting vapor from the volume for disbursement into the region within which the system is employed. Such "sub-pressure generators" may exhibit a wide variety of configurations, their function being to derive the noted lowered pressure. A variety of such generators will occur to those art skilled, for instance fan or compressor based systems, pumps, plunger-type mechanisms, differentially weighted tubing, heat by convection and the like.

The sub-pressure generator may be implemented utilizing an airflow generator such as an electric motor driven fan in conjunction with a variety of system architectures. In one such system an airflow passageway having a venturi tube-defining constricted region is located downstream of the fan outlet and cooperates with a vapor delivery channel which is extensible into the region above the fragrance liquid surface. This creates the requisite lower pressure to enhance vapor evaporation while moving vapor out of the system and into the region within which it is placed. For all embodiments, the electric motor driven fan may be powered from an a.c. source such as a common residential receptacle or from one or more batteries.

In another approach, the sub-pressure generator is configured with an evacuation chamber in vapor flow communication with the surface of the fragrance liquid and the vapor-containing volume above it. The chamber has an outlet with a fan in adjacency thereto to provide for developing a pressure lower than atmospheric pressure within the chamber and thus, at the surface of the fragrance liquid. Performance of the evacuation chamber can be enhanced by adding a bubbling feature to it.

The bubbling feature may be further implemented in a positive pressure manner by incorporating it within the entry portion of above-noted airflow passageway, for example, by providing an inlet to the bubbling components downstream of the electric motor driven fan and upstream from the evacuation channel extending from the constricted portion of the passageway.

Still another embodiment of the invention employs a convection chamber with an electrically energized heating assemblage which is positioned above the fragrance fluid receptacle and communicates with convective air and vapor movement through an evacuation channel to an outlet.

For all of the embodiments, the amount of lowered pressure at the fragrance fluid interface surface may be adjusted with an air inlet channel in airflow communication between atmospheric air and the vapor-containing volume above the fluid interface. A valve may be provided which is adjustable to control airflow within that channel.

Another feature and object of the invention is to provide a method for emanating fragrance vapor into a region exhibiting atmospheric pressure, comprising the steps:
(a) providing a receptacle having an internal cross-section-defining liquid-vapor interface area and extending to an access opening;
(b) locating a fragrance liquid within the receptacle in a manner providing a liquid phase surface corresponding with the interface area and defining a vapor-containing volume thereabout in gas flow communication with the receptacle access opening; and
(c) communicating the vapor volume with the region while deriving a lower pressure less than the atmospheric pressure at the liquid phase surface.

Another feature and object of the invention is to provide a method for emanating fragrance vapor into a region exhibiting given atmospheric pressure, comprising the steps:
(a) providing a receptacle having an internal cross-section-defining liquid-vapor interface area;
(b) locating a fragrance liquid within the receptacle in a manner providing a liquid phase surface corresponding with the interface area when in a quiescent state;
(c) directing a flow of air into one or more locations beneath the liquid phase surface an amount sufficient to generate bubbles effective to provide an effective area greater than the interface area enhancing vaporization therefrom; and
(d) directing vapor from the effective area into the region.

Other objects of the invention will, in part, be obvious and will, in part, appear hereinafter. The invention, accordingly, comprises the system and method possessing the construction, combination of elements, arrangement of parts and steps which are exemplified in the following detailed description.

For a fuller understanding of the nature and objects of the invention, reference should be had to the following detailed description taken in connection with the accompanying drawings.

BRIEF DESCRIPTION OF THE DRAWINGS

FIG. 1 is a perspective view of a fragrancing system and method according to the invention;

FIG. 2 is a sectional view taken through the plane 2-2 shown in FIG. 1;

FIG. 3 is a side partially sectional view of another embodiment of the system and method of the invention;

FIG. 4 is a side, partially sectional view of another embodiment of the system and method of the invention;

DETAILED DESCRIPTION OF THE INVENTION

Figure 5:
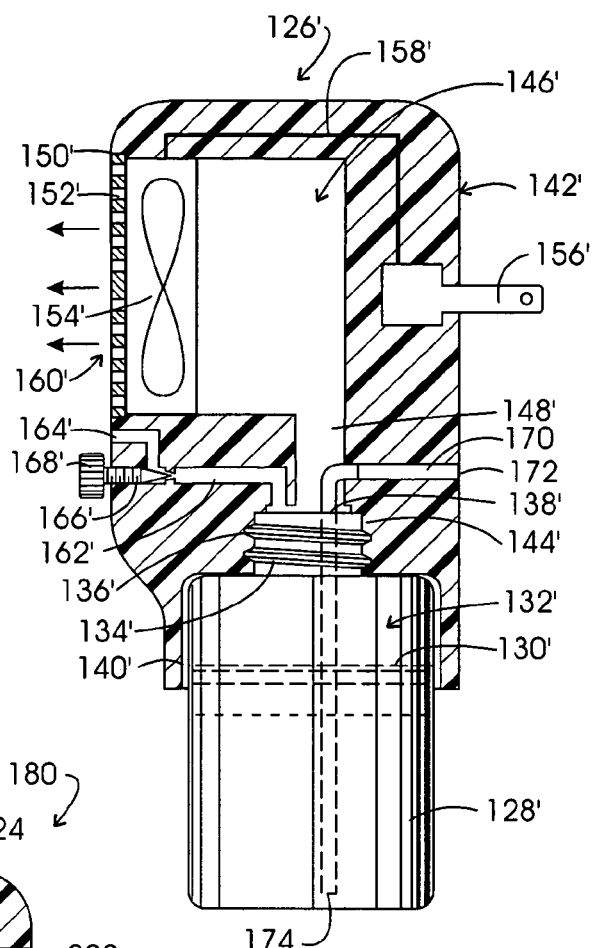
FIG. 5 is a partially sectional side view illustrating an adaptation of the embodiment of FIG. 4 to incorporate a bubbling feature.

In the discourse to follow, the embodiments of a fragrancing system and method are described. Each such embodiment involves a liquid fragrance phase and an evaporation-evoked fragrance vapor or gaseous phase. Vaporization of a liquid below its boiling point generally is referred to as evaporation. Those molecules of a liquid having the highest probability of escaping or evaporating into the vapor phase are the surface molecules. The rate of such evaporation generally is dependent upon the instantaneous concentration of vapor molecules within the volume above the liquid surface. Thus, by decreasing the vapor molecule population by lowering pressure below atmospheric pressure to evolve a partial pressure with air, evaporation may be increased. Similarly, since evaporation is a surface phenomena, an increase in the surface area of a fragrance liquid will result in an increase in the number of surface molecules such that more will escape into the vapor state, not withstanding that changing surface area will not affect vapor pressure itself. A technique for expanding the surface area without changing the cross-section of a liquid receptacle is achieved by creating bubbles within the liquid phase. These bubbles, in effect, evoke an effective surface area which is greater than the surface area of the fluid in a quiescent state.

The above considerations may be supported by observations stemming from Raoult's Law:

$$p_A = y_A P = x_A p^*_A(T)$$

Here $p_A$ is the partial pressure of component A above the liquid, $y_A$ is the mole fraction of A in the gas phase, P is the system pressure, $X_A$ is the mole fraction of component A in the liquid phase and $p^*_A$ is the vapor pressure of the pure liquid A at temperature T. This equation explains a system with multiple components in equilibrium between its liquid and vapor phase.

Each component (A, B, C . . . n) will have similar expressions in this system, where all the partial pressures ($p_A$, $p_B$, $p_C$ . . . $p_N$.) add up to the total pressure (P) on the system.

If we choose components for the formula with similar volatility (no weigh agents or high molecular weight components), in other words, all components having similar $p^*$'s, we can treat all the components as A and $x_A=1$, in this expression. Now the equation becomes . . .

$$p_A = y_A P = p^*_A(T)$$

Once all the air components are removed from above the liquid, $y_A$ approaches one and the expression becomes $p_A = P = p^*_A(T)$.

In a dynamic system, where component A in the vapor phase is constantly being removed (using the vacuum, pump or fan), more of the component A will move from the liquid phase to the gas phase, to maintain equilibrium. When the system is closed, the pressure (P) is reduced; the system will now try to increase the pressure above the liquid by moving more of the components into the vapor phase to maintain equilibrium. The system will naturally try to maintain a pressure of $p^*_A$ (T) above the liquid. This is why liquids boil at a lower temperature at higher altitudes (low pressure).

Of course, during this process, the temperature (T) of the system will drop (evaporative cooling) temporarily but will move back to room temperature since the system is not insulated from the environment. As long as the pressure reducing force is maintained above the liquid, evaporation rate will be higher than normal conditions.

The faster the system tries to re-establish equilibrium the higher the rate of evaporation. A way to help drive the system to equilibrium is to increase the liquid to vapor interface. One way to do this is to incorporate a bubbler.

Referring to FIG. 1, an initial embodiment of a system for emanating fragrance vapor into a region such as the room of a home is represented generally at 10. The apparatus incorporated with system 10 includes a fragrance liquid phase receptacle 12 which is threadably connected with a sub-pressure generator represented generally at 14. Other attachment approaches will be apparent to those skilled in the art. Generator 14 is formed of a polymeric material and is configured to be plugged into a conventional wall outlet. When so energized, fragrance vapor is driven into the region receiving fragrance vapor through a grill 16. User adjustment of the amount of fragrance vapor is provided by hand manipulation of a small valve knob 18 which will be seen to perform in conjunction with an air inlet channel, the opening of which to atmospheric air in the region is shown at 20.

Looking to FIG. 2, receptacle 12 reappears. The cylindrical body of receptacle 12 exhibits an internal cross-section which defines a liquid-vapor interface area in a quiescent state. A fragrance liquid is retained within the receptacle 12 and exhibits a liquid phase surface shown in phantom at 22 which corresponds with the noted internal cross-section. Above the liquid phase surface 22 is a vapor-containing volume represented generally at 24. In the course of evaporative use of system 10, the level 22 will vary and, in turn, so will the volume 24. Located upwardly from the liquid phase surface 22 and volume 24 is an access opening 26 which is configured as a threaded neck. Receptacles as at 12 may be fashioned of a polymeric material, glass, metal or the like and generally are configured to enhance the marketing of the fragrance liquids. Generator 14 is seen to be configured with a lower disposed receptacle-receiving cavity 28. Extending centrally upwardly from cavity 28 is an internally threaded connector cavity 30 which engages the external threads 32 of the neck of receptacle 12. Extending across the generator 14 is an airflow passageway represented generally at 34. Passageway 34 is formed having an air input 36 and extends inwardly to a venturi tube-defining constricted portion 38, whereupon the passageway expands in cross-sectional area to an output 40. An airflow generator represented symbolically as an electric motor-driven fan is shown at 42 located adjacent the passageway input 36. While other sources of airflow can be employed, the small inexpensive and practical fan as represented at 42 is preferred. As represented at downstream arrow array shown generally at 44, the device at 42 provides an airflow into and across the constricted region 38 and thence through the output 40.

Extending in gas flow communication between airflow passageway 34 and access opening 26 of receptacle 12 within cavity 28, is a vapor delivery channel represented generally at 46. Channel 46 is configured having a downstream directed vapor outlet 48 located centrally within the constricted portion 38 of airflow passageway 34. Delivery channel 46 then extends to cavity 30 and gas flow communication with volume 24 and the associated liquid phase surface 22. With the arrangement, the enhanced air velocity at constricted portion 38 will pass over vapor outlet 48 to, in turn, cause the pressure within passageway 46 and thus volume 24 to decrease below atmospheric pressure and effect a lowered pressure at the liquid phase surface 22 to enhance evaporation of vapor therefrom. In effect, the passageway 46 with vapor outlet 48 performs in the manner of a pitot tube. As noted-above, removal of fragrance vapor also promotes evaporation at liquid surface 22. a conventional embedded electric plug is shown at 50 incorporated within the generator 14. Leads extending to an electric motor associated with the fan at 42 are represented at a line 52.

The amount of sub-atmospheric pressure provided at volume 24 can be regulated utilizing the earlier-described valve knob 18 which performs in conjunction with an air inlet channel represented generally at 54 which extends from the opening 20 to cavity 30 and thus through access opening 26 for communication with volume 24. The extent of atmospheric air permitted to flow into the channel 54 through opening 20 is regulated by a needle valve 56 which is maneuvered from knob 18.

An advantage in terms of cost and performance is realized with the utilization of the evaporation approach to fragrance vapor emanation. In this regard, the fragrance liquid within receptacles as at 12 may be provided without the addition of evaporation inhibitor agents such as glycol ether. In general, emulsification agents also are not required for maintaining a uniform mixture throughout fragrance liquid shelf life. The operational function of systems 10 being to enhance evaporation, providing fragrance liquids substantially devoid of such agents promotes system performance. Also, the fragrancing process can be enhanced by adding higher volatile components to increase average vapor pressure in the system without substantially detracting from the quality of fragrance (low fragrance impact). Generally, the resultant fragrance liquid will exhibit low concentrations of low molecular weight alcohols such as ethanol or isopropyl alcohol. The specific levels of these solvents will depend upon the overall formula, flash point and the like.

Referring to FIG. 3, another embodiment of the fragrancing system is represented in general at 60. System 60 is quite similar to system 10. However, battery power is supplied to an electric motor-driven fan and the effective area of the fragrance liquid interface surface is developed having value greater than such surface would have in a quiescent state. A cylindrically-shaped receptacle similar to that at 12 is shown at 62 retaining a fragrance fluid exhibiting a given liquid phase surface 64 above which a vapor-containing volume shown generally at 66 extends to a connector neck 68 having an access opening 70 and external threads 72. When in a quiescent state the area exhibited by liquid phase surface 64 will correspond with the internal cross sectional area of receptacle 62. External threads 72 engage the internal threads of an internally threaded connector cavity 74 of a sub-pressure generator represented generally at 76. System 60 will have an external appearance identical to system 10 as represented in FIG. 1. The system incorporates an airflow passageway represented generally at 78 having an air input 80; a centrally disposed constricted portion 82; and an output 84. A grill 86 is located at output 84 and an airflow generator implemented with a d.c. electric motor-driven fan 88 is seen to be located adjacent input 80. Fan 88 is powered from one or more batteries, two of which are seen at 90 and 92 within a battery compartment 94. Batteries 90 and 92 are operationally associated with the fan 88 through a hand actuated switch 96, the leads extending from switch 96 being represented by two leads shown generally at 98. System 60 also can be powered from an a.c. outlet in the manner of system 10, while the latter system 10 may be battery powered as shown in connection with system 60. An advantageous feature of the battery powering arrangement is that the system may be positioned upright on a table or shelf and located essentially where ever the user desires. The airflow generating function of fan 88 derives a downstream airflow along passageway 78 as represented by the arrow array shown generally at 100. Velocity of this downstream airflow, as before, will be increased at the constricted portion 86 of passageway 78. A vapor delivery channel represented generally at 102 is shown extending from a downstream oriented vapor outlet 104 within constricted portion 82. Channel 102 is in gas flow communication with vapor-containing volume 66 through the receptacle access opening 70. Accordingly, with this arrangement, upon energization of fan 88, airflow within restricted portion 82 of pathway 78 flows over the opening 104 to evoke a pressure lower than atmospheric pressure which is witnessed at vapor-containing volume 66 as well as at the liquid phase interface surface 64. With system 60, this lower pressure is employed, inter alia, to generate bubbles extending through liquid phase interface surface 64. In this regard, a bubbler passageway represented generally at 106 stems from input 108 in communication with atmospheric air to one or more outlets as at 110 within the liquid phase. With this arrangement, when the liquid phase surface 64 is in a quiescent state it will exhibit an area corresponding with the internal cross-sectional area of receptacle 62. However, with the generation of bubbles that surface area will increase to provide what is herein termed as an "effective area" which is larger than the area in a quiescent state. As noted-above, while vapor pressure does not change this arrangement, a greater area is presented for vapor molecule escape from the surface of the fragrance liquid.

To regulate the extent of lowered pressure within the vapor-containing volume 66 an air inlet channel is provided as represented in general at 112 extending from an opening 114 configured for receiving atmospheric air and vapor-containing volume 66 via receptacle access opening 70. Control over the ingress of atmospheric air into channel 112 is provided by a needle valve 116 which, in turn, is hand actuable via valve knob 118.

As in the case of system 10, the sub-pressure generator 76 may be formed of a polymeric material, while the receptacle 62 may be formed of polymeric material, glass, metal or the like.

Referring to FIG. 4, the instant system and method is seen implemented as represented in general at 126 with an evacuation chamber approach. The figure reveals a cylindrically-shaped receptacle 128 containing a fragrance liquid having a liquid phase surface represented in phantom at 130. A vapor containing volume is represented in general at 132 above surface 130. Receptacle 128 extends with an integrally-formed neck having external threads 136 to an access opening 138. Note that receptacle 128 is positioned within a receptacle-receiving cavity 140 of a sub-pressure generator represented generally at 142. In this regard, the generator 142 incorporates an internally threaded connector cavity 144 which threadably engages the external threads 136 of receptacle neck 134. Generator 142 is configured having an evacuation chamber represented generally at 146 with an input channel 148 extending in gas flow exchange relationship with the vapor-containing volume 132 and interface surface 130 through access opening 138. Chamber 146 is formed with a relatively large diameter output 150 which is covered by a grill 152 structured in a manner of grill 16 (FIG. 1). Positioned adjacent output 150 is an airflow generator implemented as an electric motor-driven fan represented at symbol 154. Fan 154 is represented as being powered from an a.c. electrical source available at a conventional a.c. receptacle utilizing an embedded plug 156. Leads from plug 156 are represented symbolically at line 158 extending to fan assemblage 154. With the arrangement shown, upon energization of the fan 154 an airflow represented at arrow array 160 is derived causing chamber 146 to assume a pressure below atmospheric pressure. That partial pressure is provided at vapor-containing volume 132 and liquid interface surface 130 to promote evaporation as well as dispersion of vapor through the output 150. Regulation of the sub-atmospheric pressure is provided from an air inlet channel represented generally at 162 extending from cavity 140 to an opening 164. Control over atmospheric air ingress into channel 162 is provided by a needle valve 166 which is adjusted from valve knob 168.

System 126 also can be configured to perform in conjunction with a bubbler passageway. Looking to FIG. 5 system 126 again is portrayed with components repeated from FIG. 4 being represented by the same identifying numeration but in primed fashion. Thus, system 126' performs in conjunction with a cylindrical receptacle 128' having a liquid phase surface 130' shown in phantom. Above the surface 130' is a vapor-containing volume 132' which extends to a neck 134' having external threads 136' and an access opening 138'. Receptacle 128' is retained within a receptacle-receiving cavity 140' of sub-pressure generator 142'. Connection again is provided by engagement of the external threads 136' of neck 134' with the internal threads of a connector cavity 144'. Sub-pressure generator 142' is configured with an evacuation chamber represented generally at 146' having an input channel 148' communicating in gas flow relationship with vapor-containing volume 132' and surface 130' and an output 150'. A grill 152' covers the output 150' and an electric motor-driven fan is provided adjacent output 150' as represented at symbol 154'. Fan assemblage 154' is powered from a conventional a.c. receptacle through the utilization of an embedded plug 156', the electrical leads from which extend to the fan assemblage 154' as represented at line 158'. Accordingly, upon energization of electric motor-driven fan 154' vapor is driven through outlet 150' as represented by the arrow array shown generally at 160'. For the instant embodiment in similar fashion as system 60, a bubbler passageway 170 is seen to extend from an inlet 172 in airflow communication with the environmental region within which the system 126' is located and one or more bubbler outlets as represented at 174 located within the liquid phase. Accordingly, as the operation of fan assemblage 154' lowers the pressure within evacuation chamber 146' to a level below atmospheric pressure, vapor will be drawn from vapor-containing volume 132' and the effective surface area of the liquid-vapor interface developed with bubbles. Thus, vapor molecules are removed to enhance evaporation and the area of the vapor/liquid interface is expanded by bubbles to permit more vapor molecules to escape from the surface.

Sub-atmospheric pressure at the vapor-containing volume 132' and at the interface surface of effective area is adjustable from an air inlet channel 162' which is in airflow communication with atmospheric air within the region or environment of system 126' at opening 164. The amount of air ingressing through opening 164' is adjusted by needle valve 166' which, in turn, is adjustable from valve knob 168'. With the arrangement, adjustment can be made such that the principal creation of fragrance vapor is in consequence of the expanded interface effective area evaporatively performing in conjunction with removal of vapor molecules within the volume 132'.

Figure 6:
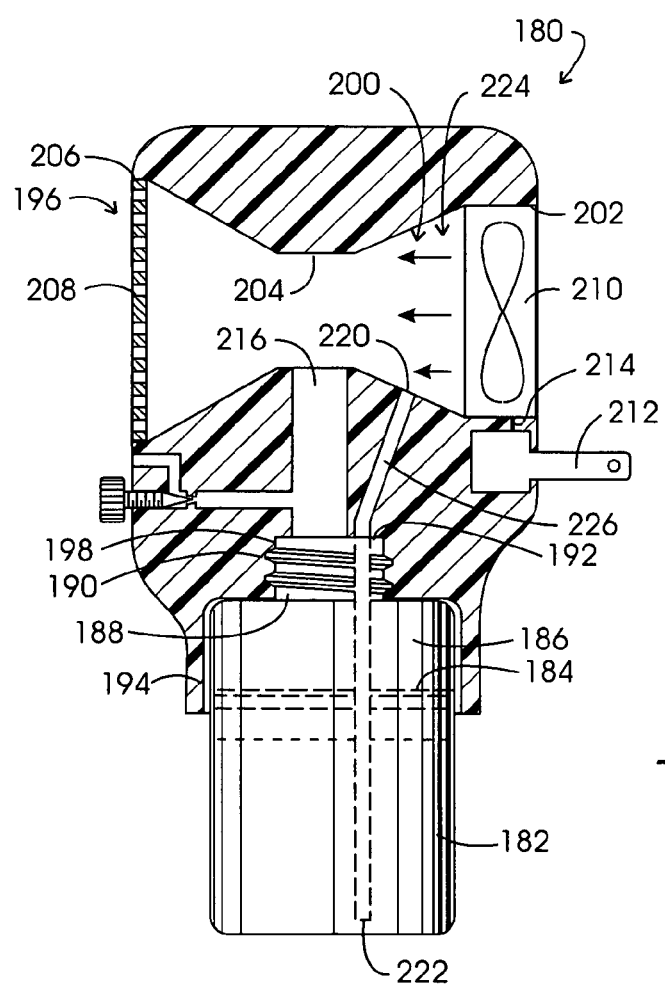
FIG. 6 is a side partially sectional view of another embodiment of the invention.

The bubbler function also can be incorporated in conjunction with a pressurized air input combined with a vapor molecule evacuation arrangement. Looking to FIG. 6, a fragrance vapor emanating system is represented in general at 180. System 180 incorporates a cylindrically-shaped liquid fragrance receptacle 182 which contains fragrance liquid with a liquid phase surface shown in phantom at 184 having an area corresponding with the internal cross-sectional area of receptacle 182 when in a quiescent state. Above the interface 184 is a vapor-containing volume 186 which communicates with a receptacle neck 188 having external threads 190. The access opening of receptacle 182 is shown at 192.

Receptacle 182 is shown retained within a receptacle access opening 194 formed within the lower portion of a sub-pressure generator represented generally at 196. Connection with device 196 is provided at an internally-threaded connector cavity 198 which receives the receptacle neck 188 and engages external threads 190.

Extending across the device 196 is an airflow passageway represented generally at 200 having an air input 202, and a downstream constricted portion from which the passageway expands toward an output 206. A grill 208 is mounted across output 206 and an airflow generator in the form of an electric motor-driven fan represented at symbol 210 is located adjacent air input 202. The electric motor of fan assemblage 210 may be powered from batteries in the manner of FIG. 3 or from a conventional a.c. receptacle. For the latter arrangement an embedded plug as represented at 212 may be utilized. The electrical association between plug 212 and the assemblage 210 is represented at line 214. Driven air movement is represented at arrow array 224. An evacuation channel 216 extends from airflow passageway 200 at the constricted region 204 to the access opening 192 of receptacle 182. Note that this evacuation channel is of larger diameter, for instance, than the downstream directed vapor delivery channel 46 shown in FIG. 2. While a lowered pressure at vapor-containing volume 186 and interface surface 184 is developed it is of lesser value than the lower pressure derived in the embodiments of FIGS. 2 and 3. However, the device 196 incorporates a bubbler passageway represented in general at 226 having an inlet 220 located within the airflow passageway 200 in the vicinity of input 202 and preferably at a location between input 202 and the commencement of the restricted portion 204. With such positioning of the inlet 220 a positive pressure is asserted into bubbler passageway 226 which extends to one or more outlets as at 222 within the fragrance liquid phase. The resultant created bubbles derive an effective liquid surface area greater than the internal cross-section defining liquid-vapor interface area otherwise provided at 184 when in a quiescent state with no bubbles being produced. This larger effective area while not altering vapor pressure permits the escape of more vapor molecules into the vapor-containing volume 186 which are removed by the action of airflow as represented at arrow array 224 over evacuation channel 216 as it opens at constricted portion 204 of passageway 200.

Figure 7:
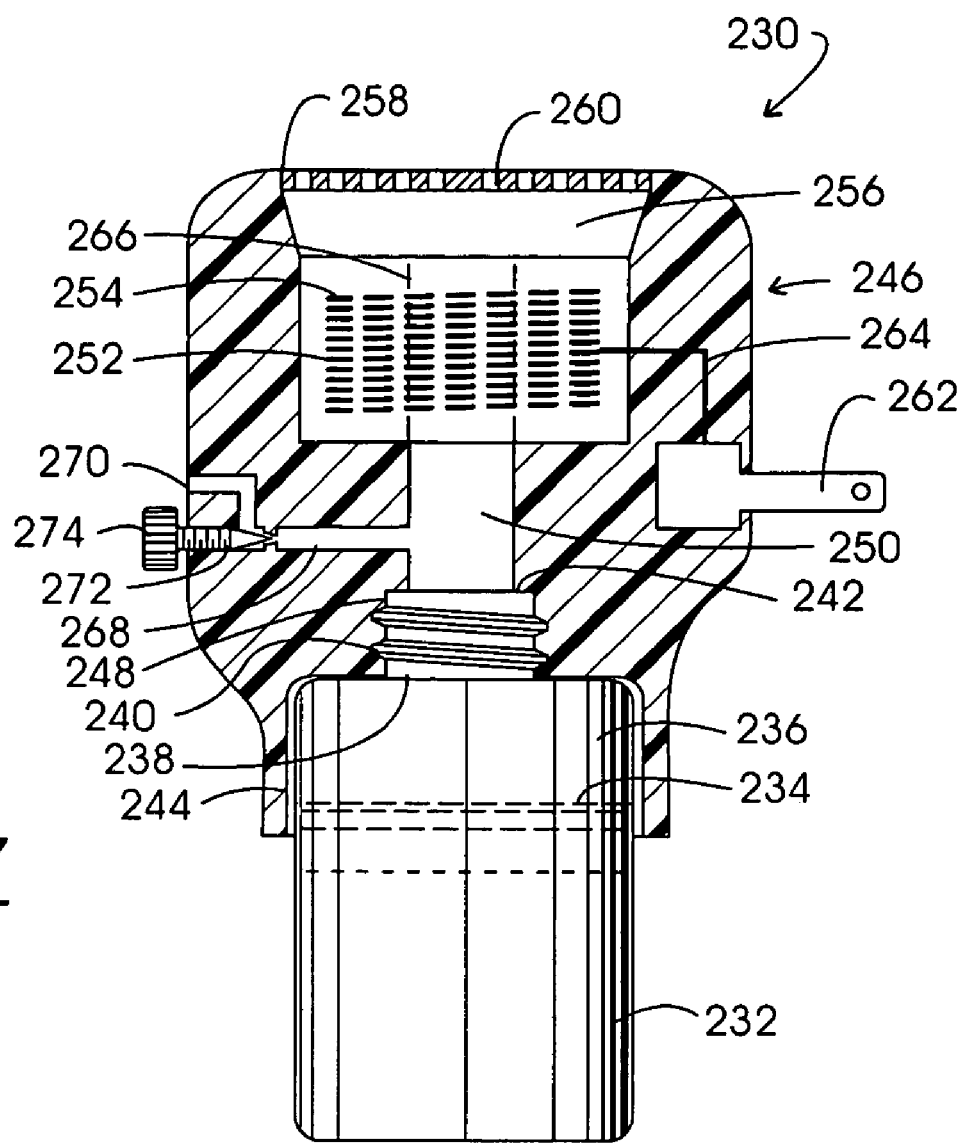
FIG. 7 is a side partially sectional view of another embodiment of the invention.

A lowering of pressure at the liquid phase interface and within the vapor-containing volume also can be realized through the utiliization of a convection chamber. Referring to FIG. 7, such a system is represented in general at 230. As before, system 230 incorporates a receptacle containing a fragrance liquid having a given liquid phase surface or interface surface represented in phantom at 234 above which is a vapor molecule containing volume 236. Container 232 extends upwardly to define a neck 238 carrying integrally-formed external threads 240 and extending to an access opening 242. Receptacle 232 is retained within the receptacle-receiving cavity 244 of a sub-pressure generator represented generally at 246. Connection between the receptacle 232 and generator 246 is at an internally threaded connector cavity 248 which functions to engage external threads 240. Cavity 248 is configured in gas flow communication between vapor-containing volume 236 and liquid interface surface 234 by an evacuation channel 250 extending, in turn, to a convection chamber represented generally at 252. Chamber 252 supports an electrically resistive heater coil assembly 254. Extending upwardly from the assembly 254 is an outwardly expanding annular outlet region 256 which, in turn, extends to an annular output 258 over which a grill 260 is positioned. Heater assembly 254 incorporates an outwardly disposed thermally insulative jacket (not shown) which may be fashioned of a ceramic or the like and is energized from a conventional a.c. receptacle from an embedded electrical plug 262. Electrical communication with the heater assembly 254 is represented at lead line 264. As represented in phantom at 266 the evacuation channel may be extended through the heating assembly 252 to the annular outlet region 256 depending upon the desires of the designer.

With the arrangement shown, the air is heated by the assembly 252 to evoke a convective movement thereof through outlet 258. This will create a pressure lower than atmospheric pressure within vapor-containing volume 236 and at the liquid interface surface 234 to remove vapor molecules and enhance evaporation of fragrance vapor into the region within which system 230 is located. That lower pressure may be adjusted, as before, at an air inlet channel represented generally at 268 having an ambient air inlet opening 270 and extending in air transfer relationship to the evacuation channel 250. Control over the air input to channel 268 is provided by a needle valve 272 which, in turn, is manually controlled by a valve knob 274.

Since certain changes may be made in the above-described system and method without departing from the scope of the invention herein involved, it is intended that all matter contained in the description thereof or shown in the accompanying drawings shall be interpreted as illustrative and not in a limiting sense.

The invention claimed is:

1. A system for emanating fragrance vapor into a region exhibiting given atmospheric pressure, comprising:
   a receptacle having an internal cross-section defining liquid-vapor interface area, and extending to an access opening;
   a fragrance liquid phase within said receptacle having a liquid surface corresponding with said interface area and defining a vapor volume thereabove in gas flow communication with said access opening;
   a sub-pressure generator connectable in gas flow communication with said vapor volume through said access opening, and energizable to derive a lowered pressure below said given atmospheric pressure at said liquid surface effective to enhance the evaporative generation of a vapor phase above said liquid surface and at least the partial disbursement thereof through said access opening and into said region
   said sub-pressure generator further comprising:
   an evacuation chamber in vapor flow communication with said vapor volume from said receptacle access opening and having a chamber outlet to said region; and
   a fan located adjacent said chamber outlet actuable to lower pressure with said chamber to an extent deriving said lowered pressure; and
   further comprising:
   a bubbler passageway extending from an inlet in airflow communication with said region and a bubbler outlet located within said liquid phase and effective to create bubbles expanding the effective area of said liquid surface.

2. A system for emanating fragrance vapor into a region exhibiting given atmospheric pressure, comprising:
   a receptacle having an internal cross-section defining liquid-vapor interface, area, and extending to an access opening;
   a fragrance liquid phase within said receptacle having a liquid surface corresponding with said interface area and defining a vapor volume thereabove in gas flow communication with said access opening;
   a sub-pressure generator connectable in gas flow communication with said vapor volume through said access opening, and energizable to derive a lowered pressure below said given atmospheric pressure at said liquid surface effective to enhance the evaporative generation of a vapor phase above said liquid surface and at least the partial disbursement thereof through said access opening and into said region; and
   said sub-pressure generator further comprising:
   an airflow passageway having an air input, a venturi tube-defining constricted portion spaced from said input and an output;
   an airflow generator adjacent said passageway input and energizable to provide a flow of air downstream from said input, across said constricted portion and through said output; and
   a vapor delivery channel extensible in gas flow communication between said receptacle access opening and said airflow passageway constricted portion and having a downstream directed vapor outlet configured to effect derivation of said lowered pressure.

3. The system of claim 2 further comprising:
   an air inlet channel in airflow communication between said region and said receptacle access opening; and
   a valve, adjustable to control the flow of air within said air inlet channel.

4. The system of claim 2 in which
   said airflow generator is an electric motor-driven fan energizable from a source of power.

5. The system of claim 4 in which:
   said sub-pressure generator is configured to provide said source of power from an a.c. plug receptacle.

6. The system of claim 4 in which:
   said sub-pressure generator is configured to provide said source of power from one or more batteries.

7. The system of claim 2 further comprising:
   a bubbler passageway extending from an inlet in airflow communication with said region and one or more bubbler outlets located within said liquid phase and effective to derive a bubble created effective liquid surface area greater than said internal cross-section defining liquid-vapor interface area.

8. The system of claim 7 in which:
   said bubbler passageway inlet is located in the vicinity of said airflow passageway air input.

9. The system of claim 2 further comprising:
   a bubbler passageway extending from an inlet located within said airflow passageway at a location effective to cause a positive pressurized airflow therein and having one or more bubbler outlets located within said liquid phase effective to derive a bubble created liquid surface effective area greater than said internal cross-section defining liquid-vapor interface area.

10. The system of claim 9 in which:
    said bubbler passageway inlet is located between said airflow passageway air input and said constricted portion.

11. A system for emanating fragrance vapor into a region exhibiting given atmospheric pressure, comprising:

a receptacle having an internal cross-section defining liquid-vapor interface area, and extending to an access opening;

a fragrance liquid phase within said receptacle having a liquid surface corresponding with said interface area and defining a vapor volume thereabove in gas flow communication with said access opening;

a sub-pressure generator connectable in gas flow communication with said vapor volume through said access opening, and energizable to derive a lowered pressure below said given atmospheric pressure at said liquid surface effective to enhance the evaporative generation of a vapor phase above said liquid surface and at least the partial disbursement thereof through said access opening and into said region, said sub-pressure generator further comprising:

an evacuation chamber in vapor flow communication with said vapor volume from said receptacle access opening and having a chamber outlet to said region; and a fan located adjacent said chamber outlet actuable to lower pressure within said chamber to an extent deriving said lowered pressure;

said system further comprising:

an air inlet channel in airflow communication between said region and said receptacle access opening; and a valve, adjustable to control the flow of air within said air inlet channel.

12. A system for emanating fragrance vapor into a region exhibiting given atmospheric pressure, comprising:

a receptacle having an internal cross-section defining liquid-vapor interface area, and extending to an access opening;

a fragrance liquid phase within said receptacle having a liquid surface corresponding with said interface area and defining a vapor volume thereabove in gas flow communication with said access opening;

a sub-pressure generator connectable in gas flow communication with said vapor volume through said access opening, and energizable to derive a lowered pressure below said given atmospheric pressure at said liquid surface effective to enhance the evaporative generation of a vapor phase above said liquid surface and at least the partial disbursement thereof through said access opening and into said region; and in which said sub-pressure generator further comprises:

a convection chamber in vapor flow communication with said vapor-containing volume from said receptacle access opening and having a convection outlet to said region; and a heat exchanger energizable adjacent said convection outlet from a source of electrical power to heat air in heat exchange communication therewith to an extent effective to derive said lowered pressure.

13. The system of claim 12 further comprising:

an air inlet channel in airflow communication between said region and said receptacle access opening; and a valve, adjustable to control the flow of air within said air inlet channel.

14. The system of claim 12 in which:

said sub-pressure generator is configured to provide said source of electrical power from an a.c. plug receptacle.

15. A method for emanating fragrance vapor into a region exhibiting given atmospheric pressure, comprising the steps:

(a) providing a receptacle having an internal cross-section-defining liquid-vapor interface area and extending to an access opening;

(b) locating a fragrance liquid within said receptacle in a manner providing a liquid phase surface corresponding with said interface area and defining a vapor-containing volume thereabout in gas flow communication with said receptacle access opening;

(c) communicating said vapor volume with said region while deriving a lower pressure less than said atmospheric pressure at said liquid phase surface, said step (c) being carried out by:

providing a vapor delivery channel in gas flow communication between said access opening and a vapor outlet;

directing an airflow across said vapor outlet at a velocity and direction effective to derive said lower pressure;

said step (c) being further carried out by:

providing an air inlet channel in airflow communication between said region and said vapor-containing volume; and controlling the extent of said lower pressure by adjusting the amount of said airflow communication.

16. A method for emanating fragrance vapor into a region exhibiting given atmospheric pressure, comprising the steps:

(a) providing a receptacle having an internal cross-section-defining liquid-vapor interface area and extending to an access opening;

(b) locating a fragrance liquid within said receptacle in a manner providing a liquid phase surface corresponding with said interface area and defining a vapor-containing volume thereabout in gas flow communication with said receptacle access opening;

(c) communicating said vapor volume with said region while deriving a lower pressure less than said atmospheric pressure at said liquid phase surface, said step (c) being carried out by:

providing a vapor delivery channel in gas flow communication between said access opening and a vapor outlet;

directing an airflow across said vapor outlet at a velocity and direction effective to derive said lower pressure; and said step (c) is further carried out by:

providing an airflow passageway having an air input, a downstream constricted region extending across said vapor delivery channel, and an output; and directing said airflow from said air input downstream through said constricted region and through said output into said region.

17. The method of claim 16 in which said step (c) is further carried out by:

aligning said vapor delivery channel vapor outlet to face substantially downstream within said directed airflow.

18. The method of claim 16 in which said step (c) is further carried out by:

providing an electric motor-driven fan energizable from an a.c. source of power adjacent said airflow passageway air input; and energizing said electric motor-driven fan from said source.

19. The method of claim 16 in which said step (c) is further carried out by:

providing an electric motor-driven fan energizable from a d.c. source of power adjacent said airflow passageway air input.

20. A method for emanating fragrance vapor into a region exhibiting given atmospheric pressure, comprising the steps:

(a) providing a receptacle having an internal cross-section-defining liquid-vapor interface area and extending to an access opening;
(b) locating a fragrance liquid within said receptacle in a manner providing a liquid phase surface corresponding with said interface area and defining a vapor-containing volume thereabout in gas flow communication with said receptacle access opening;
(c) communicating said vapor volume with said region while deriving a lower pressure less than said atmospheric pressure at said liquid phase surface;
said step (c) being carried out by:
providing an evacuation chamber in vapor flow communication with said vapor-containing volume;
evacuating air from said chamber into said region to an extent deriving said lower pressure of said liquid phase surface;
said step (c) further being carried out by:
providing an air inlet channel in airflow communication between said region and said vapor-containing volume; and
controlling the extent of said lower pressure by adjusting the amount of said airflow communication.

21. A method for emanating fragrance vapor into a region exhibiting given atmospheric pressure, comprising the steps:
(a) providing a receptacle having an internal cross-section-defining liquid-vapor interface area and extending to an access opening;
(b) locating a fragrance liquid within said receptacle in a manner providing a liquid phase surface corresponding with said interface area and defining a vapor-containing volume thereabout in gas flow communication with said receptacle access opening;
(c) communicating said vapor volume with said region while deriving a lower pressure less than said atmospheric pressure at said liquid phase surface;
said step (c) being carried out by:
providing an evacuation chamber in vapor flow communication with said vapor-containing volume;
evacuating air from said chamber into said region to an extent deriving said lower pressure of said liquid phase surface;
said step (c) further being carried out by:
providing said evacuation chamber as having an input in airflow communication with said receptacle access opening and having an output in airflow communication with said region;
providing an electric motor-driven fan at said evacuation chamber input energizable to evacuate air from said chamber; and
energizing said electric motor-driven fan.

22. A method for emanating fragrance vapor into a region exhibiting given atmospheric pressure, comprising the steps:
(a) providing a receptacle having an internal cross-section-defining liquid-vapor interface area and extending to an access opening;
(b) locating a fragrance liquid within said receptacle in a manner providing a liquid phase surface corresponding with said interface area and defining a vapor-containing volume thereabout in gas flow communication with said receptacle access opening;
(c) communicating said vapor volume with said region while deriving a lower pressure less than said atmospheric pressure at said liquid phase surface;
said step (c) being carried out by:
providing a convection chamber in vapor flow communication with said vapor-containing volume and with said region and having a convection outlet to said region;
providing a heat exchanger adjacent said convection outlet energizable from a source of electrical power to heat air in heat exchange communication therewith to an extent effective to derive said lower pressure; and
energizing said heat exchanger from said source.

23. The method of claim 22 in which said step (c) further is further carried out by:
providing an air inlet channel in airflow communication between said region and said vapor-containing volume; and
controlling the extent of said lower pressure by adjusting the amount of said airflow communication.

24. A method for emanating fragrance vapor into a region exhibiting given atmospheric pressure, comprising the steps:
(a) providing a receptacle having an internal cross-section defining liquid vapor interface area and extending to an access opening:
(b) locating a fragrance liquid within said receptacle in a manner providing a liquid phase surface corresponding with said interface area and defining a vapor-containing volume thereabout in gas flow communication with said receptacle access opening;
(c) communicating said vapor volume with said region while deriving a lower pressure less than said atmospheric pressure at said liquid phase surface;
said step (c) being carried out by:
providing a convection chamber in vapor flow communication with said vapor-containing volume and with said region and having a convection outlet to said region;
providing a heat exchanger adjacent said convection outlet energizable from a source of electrical power to heat air in heat exchange communication therewith to an extent effective to derive said lower pressure; and
further comprising the step:
(d) directing a flow of air to one or more locations beneath said liquid phase surface in an amount sufficient to generate bubbles to an extent effective to expand the effective area of said liquid phase surface.

25. A method for emanating fragrance vapor into a region exhibiting given atmospheric pressure, comprising the steps:
(a) providing a receptacle having an internal cross-section-defining liquid-vapor interface area and extending to an access opening;
(b) locating a fragrance liquid within said receptacle in a manner providing a liquid phase surface corresponding with said interface area and defining a vapor-containing volume thereabout in gas flow communication with said receptacle access opening;
(c) communicating said vapor volume with said region while deriving a lower pressure less than said atmospheric pressure at said liquid phase surface; and wherein
said step (c) locates a fragrance liquid within said receptacle which has one or more higher volatility additives effective to increase the vapor pressure thereof.

26. A method for emanating fragrance vapor into a region exhibiting given atmospheric pressure, comprising the steps:
(a) providing a receptacle having an internal cross-section-defining liquid-vapor interface area and extending to an access opening;
(b) locating a fragrance liquid within said receptacle in a manner providing a liquid phase surface corresponding with said interface area and defining a vapor-containing volume thereabout in gas flow communication with said receptacle access opening;

(c) communicating said vapor volume with said region while deriving a lower pressure less than said atmospheric pressure at said liquid phase surface said step (c) being carried out by:

providing an evacuation chamber in vapor flow communication with said vapor-containing volume;

evacuating air from said chamber into said region to an extent deriving said lower pressure of said liquid phase surface; and providing a bubbler passageway in airflow communication between said region and said liquid at a bubble forming location below said liquid phase surface.

* * * * *